United States Patent [19]

Petersen

[11] Patent Number: 4,985,037
[45] Date of Patent: Jan. 15, 1991

[54] UNIVERSAL MODULAR PROSTHESIS STEM EXTENSION

[76] Inventor: Thomas D. Petersen, 9680 Alto Dr., La Mesa, Calif. 92041

[21] Appl. No.: 354,792

[22] Filed: May 22, 1989

[51] Int. Cl.$^5$ ............................................. A61F 2/38
[52] U.S. Cl. .......................................... 623/20; 623/16
[58] Field of Search ...................... 623/16, 18, 20, 21, 623/22, 23

[56] References Cited

U.S. PATENT DOCUMENTS

| 4,462,120 | 7/1984 | Rambert | 623/20 |
| 4,714,471 | 12/1987 | Grundei | 623/20 |

FOREIGN PATENT DOCUMENTS

| 0189253 | 7/1986 | European Pat. Off. | 623/20 |
| 0201407 | 12/1986 | European Pat. Off. | |
| 0797680 | 1/1981 | U.S.S.R. | |
| 1285460 | 8/1972 | United Kingdom | 623/20 |

Primary Examiner—David J. Isabella
Attorney, Agent, or Firm—H. Jay Spiegel

[57] ABSTRACT

The present invention relates to a universal modular prosthesis stem extension designed to be attachable on the undersurface of a femoral or tibial standard prosthesis. The stem extension forms a part of a modular system wherein a single stem extension could be selectively attached to any one of a multiplicity of femoral or tibial components, thus reducing the amount of inventory which is necessary to be maintained by a surgeon. In the preferred embodiment of the inventive stem extension, each stem extension is designed with a 6 degree valgus inclination and is reversible for left and right patients.

16 Claims, 2 Drawing Sheets

UNIVERSAL MODULAR PROSTHESIS STEM EXTENSION

BACKGROUND OF THE INVENTION

In the field of orthopedics, a definite clinical need exists for improved stem extensions for both femoral and tibial components. Each year, more and more aailed primary total knee arthroplasties exist due to loosening, wear, or other reasons. When a total knee arthroplasty fails, removal of the primary components thereof is necessitated, which commonly results in considerable bone loss necessitating a stem fixation in the subsequent implant.

Clinical experience has shown that large stem extensions act to stabilize the prosthesis through transmission of surface stresses to the stem and consequently to the cortical bone, thereby stress shielding deficient bone in the immediate surface bearing area. Consequently, as surgical procedures evolve, larger and longer stems are being proposed for revision surgery.

The problem is complicated because anatomical variations in different patients require a surgeon to carry in inventory four to six sizes of femoral components and ten to fifteen sizes of tibial components. Further complexity is added by virtue of the fact that the femoral stem has to be at a 6 degree valgus angle to the femoral component to fit the intermedullary canal of the femur. Thus, these prosthetic components require a great number of fixed stems. One manufacturer, for example, has at least nine different femoral stem sizes ranging from 10 millimeters to 22 millimeters in diameter. Considering the fact that they also make six femoral prostheses, for each of the left and right-hand sides, it is easy to see that over one hundred sizes and shapes of fixed prostheses have to be manufactured and must be carried in inventory by the surgeon or hospital. The high expense of each prosthesis makes carrying such a large inventory of prostheses exhorbitantly expensive.

If a stem extension could be created which could fit on the undercarriage of the articular surface of any one of a multiplicity of prostheses and, further, if such a stem extension could be made reversible, the above described inventory of prostheses could be reduced to about six prostheses and nine reversible stem extensions. Clearly, having to carry an inventory of fifteen pieces is far superior to the requirement now present in the art of keeping an inventory of over one hundred prosthetic combinations.

In a further aspect, there are anatomical considerations in the design of a stem extension which make it desirable to have such a stem extension angled in the lateral plane as well as in the medial lateral plane. Ideally the distal femoral cut of the femur is at 90 degrees or perpendicular to the angular bow of the femur as seen in the lateral plane. The angle of bowing of the femur may vary from 0 up to 12 degrees. Most commonly, this angle is from 3 to 6 degrees. Thus, fitting a fixed straight stem extension into the intermedullary canal when it has a significant degree of bowing may be quite difficult. However, if a stem extension could be made which was angled with respect to the axis of the prosthesis, such a stem extension could be installed in the intermedullary canal more easily.

Further, additional complications exist in the inclusion of a stem extension in a tibial component. As is known, some instrumentation systems which are designed to measure the exact location of tibial cuts result in cutting of the top of the tibia at varying angles such as, for example, 10 degrees 7 degrees, 3 degrees, and some absolutely perpendicular. Thus, a properly designed stem extension could be used to modify a tibial component to the particular method of instrumentation at minimal cost. While most surgeons use a 3 degree sloping cut on the proximal tibia, applicant's surgical group has been using a 10 degree slope for a number of years and finds it to be advantageous in obtaining more flexion and in controlling the forward movement of the femur on the tibia when the patient is descending stairs and making other similar movements. In such a situation, of course, the prosthesis could be initially installed without the stem extension and, if a refit is necessitated, the stem extension could be easily installed.

The following prior art is known to applicant:

United States Pats. 4,404,691 to Buning, et al. and 4,578,081 to Harder, et al. disclose a modular prosthesis assembly "including a mounting component provided with a connection portion and at least two joint components of similar shape but different dimensions and which can be connected alternatively to the mounting component". The present invention differs from the teachings of these patents as providing a different means of attachment and different characteristics as to angular displacements in the various planes as compared to the teachings of these patents.

U.S.S.R. Pat. 797,680 discloses a prosthesis including a stem and a head and wherein interconnection therebetween is by virtue of a pin. This is different from the teachings of the present invention, wherein a modular system is provided with the attachment being by virtue of two pins which are of different configuration and orientation from that which is disclosed in this U.S.S.R. Patent.

European Patent 0 021 407 to Montagne discloses a femoral prosthesis wherein a single stem assembly may be attached to one of a plurality of heads by virtue of one of a multiplicity of stem extensions. This is different from the teachings of the present invention, wherein a modular approach is utilized which reduces the number of stem extensions which may be required and which has a means of attachment different from that which is disclosed in this European Patent.

SUMMARY OF THE INVENTION

The present invention relates to a universal modular prosthesis stem extension device. The invention includes the following interrelated aspects and features:

(a) In a first aspect, the present invention is specifically devised to facilitate significant reduction in the amount of inventory which a surgeon or hospital must normally carry of prosthesis components. A prosthesis such as a tibial or femoral knee prosthesis is provided on its undersurface with a mounting means specifically designed to reversibly receive a stem extension made in accordance with the teachings of the present invention.

(b) This mounting means, preferably, consists of two flat parallel walls extending upwardly from the undersurface of the prosthesis to form a generally rectangular cubic chamber therebetween. Two pairs of aligned openings are formed in these walls and are designed to removably receive mounting pins which may be slidably received therethrough. Each modular stem extension forming a part of the present invention includes attachment means designed to enmesh with the mounting means of the prosthesis to fixedly mount the stem extension thereto.

(c) This attachment means includes an arcuate slot at an end of the mounting means and a hole therethrough spaced from the arcuate slot. In mounting the modular stem extension to the prosthesis, first, a mounting pin is inserted through the pair of holes in the mounting means closest to the undersurface of the prosthesis. Thereafter, the attachment means of the modular stem extension is inserted into the chamber of the mounting means until the arcuate slot thereof is in overlying relation to the longitudinal extent of the mounting pin which has already been inserted in its pair of holes. Thereafter, the other pair of holes in the mounting means is aligned with the hole in the attachment means of the modular stem extension and the second pin is inserted through these aligned holes to fixate the stem extension in mounted position.

(d) It should be understood that the stem extension is designed to be installed on the prosthesis in one of two orientations, which orientations are rotated 180 degrees with respect to one another. The attachment means of the modular stem extension includes two flat side walls designed to slidingly engage the two flat parallel walls of the mounting means in either orientation thereof. The specific dimensions of the mounting means and the attachment means are specifically designed to allow only these two orientations of the stem extension.

(e) Each stem extension preferably has a 6 degree valgus inclination as well as a degree of superior or inferior angulation such as, for example, 2 degrees. This inclination and angulation are anatomically correct in each reversed position of the modular stem extension. More particularly, the position of the stem extension, as properly mounted on a lefthand prosthesis, is anatomically correct as is the position of the stem extension as properly mounted on a right-hand prosthesis.

(f) After the stem extension has been properly installed on the prosthesis, cement may be used to maintain the mounting pins in their inserted position In the rare instance of cementless fixation, a locking pin can be utilized.

As such, it is a first object of the present invention to provide a universal modular prosthesis stem extension system.

It is a further object of the present invention to provide such a system wherein a single stem may be used with any one of a multiplicity of prostheses.

It is a yet further object of the present invention to provide such a modular stem extension having a unique mounting means for mounting on the undersurface of a prosthesis.

It is a still further object of the present invention to provide such a system which lowers manufacturing costs and creates tremendous flexibility not previously known.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
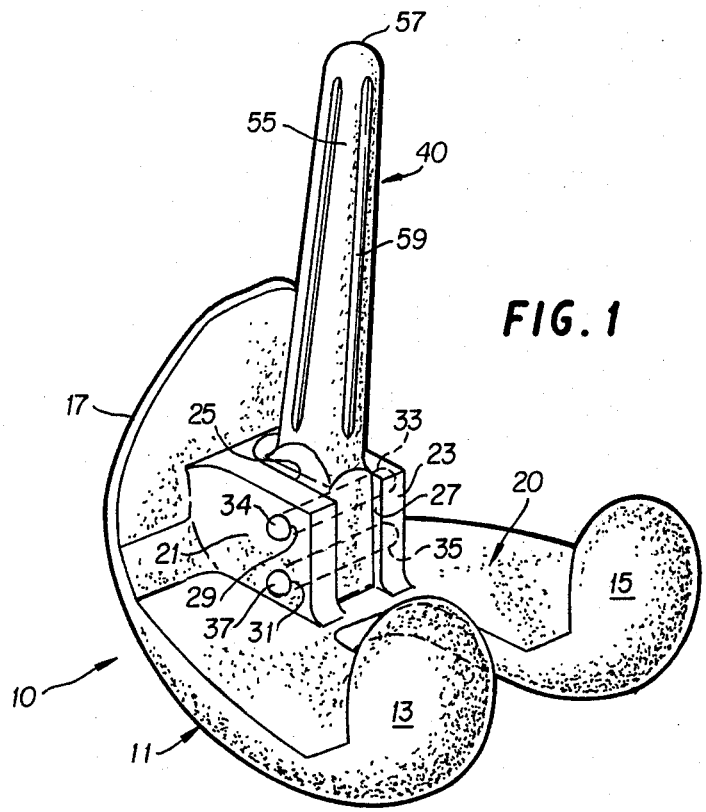
FIG. 1 shows a perspective view of a right femoral knee prosthesis.
Figure 6:
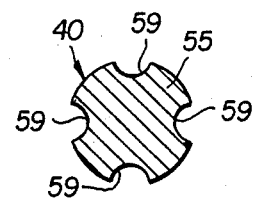
FIG. 6 shows a cross-sectional view along the line 6—6 of FIG. 5.

With reference, first, to FIGS. 1-6, a first embodiment of the present invention will be described in detail. A modular prosthesis in accordance with the teachings of the present invention is generally designated by the reference numeral 10 and is seen to include a femoral prosthetic component 11 as well as a modular stem extension therefor generally designated by the reference numeral 40. Of course, the principles and teachings of the present invention are equally applicable to any prosthetic component such as, for example, a femoral head for a hip, an acetabular. socket, a tibial knee component, and other known prostheses.

With further reference to FIGS. 1-6, it is seen that the femoral knee component 11 includes condyles 13, 15, a front surface 17, and an undersurface generally designated by the reference numeral 20.

On the undersurface 20, two parallel walls 21 and 23 are provided having respective inner flat surfaces 25 and 27 which are parallel to one another.

Figure 2:
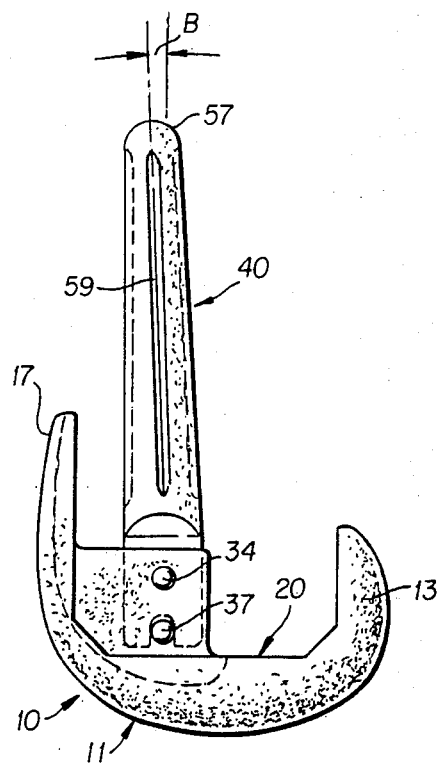
FIG. 2 shows a view from the left side of the prosthesis shown in FIG. 1.

The wall 21 includes holes 29 and 31 therethrough which are respectively aligned with holes 33 and 35 formed in the wall 23 As seen, in particular, in FIGS. 1-3, pins 34 and 37 may be inserted through respective pairs of the said holes for a purpose to be described in greater detail hereinafter.

With further reference to FIGS. 1-6, a modular stem extension 40 is seen to include a shank 41 having flat side walls 43, 45 which are designed to slidably engage the respective parallel walls 25, 27 of the walls 21, 23.

The shank 41 further includes a bottom wall 47 in which an arcuate slot 49 is cut. The shank further includes a hole 51 which is parallel to the slot 49, both of which extend between the walls 43 and 45. As should be understood from Figure 1-3 in particular, the arcuate slot 49 is designed, in assembly, to overlie the pin 37 while the hole 51 is specifically sized and configured to slidably receive therethrough the pin 34 which is also extending through the holes 29 and 33, respectively formed in the walls 21 and 23.

Figures 7, 8, 9, 10:
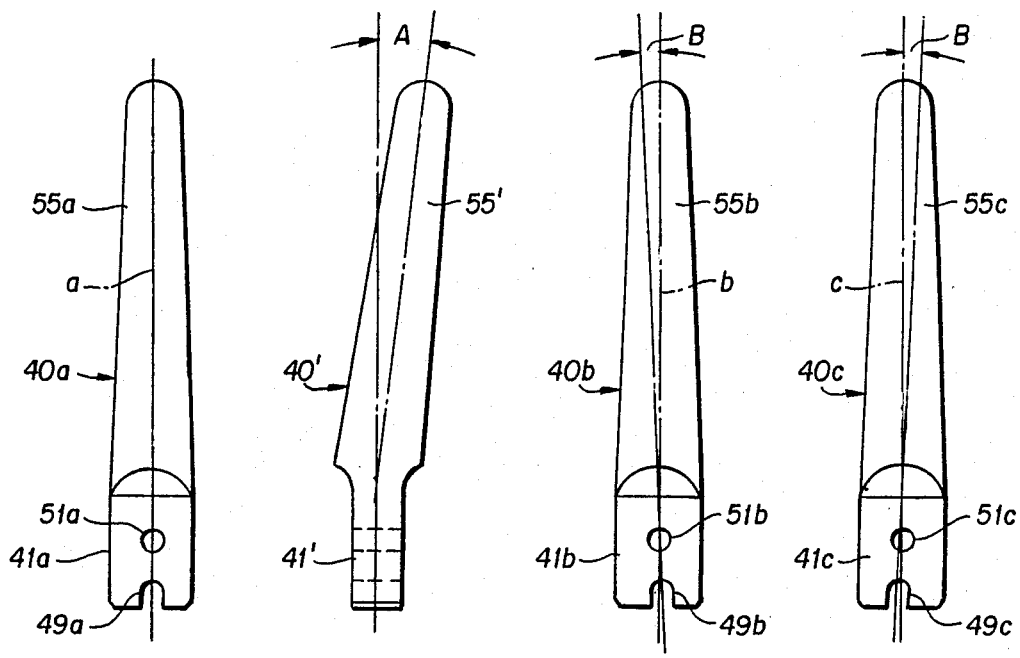
FIG. 7 shows an embodiment of modular stem extension having neutral inferior and superior angulation.
FIG. 8 shows a modular stem extension having a valgus inclination which is common to all stem extension embodiments of the present invention.
FIG. 9 shows a further embodiment of a stem extension having left inferior angulation reversible to right superior angulation.
FIG. 10 shows a modular stem extension having left superior angulation reversible to right inferior angulation.
Figure 3:
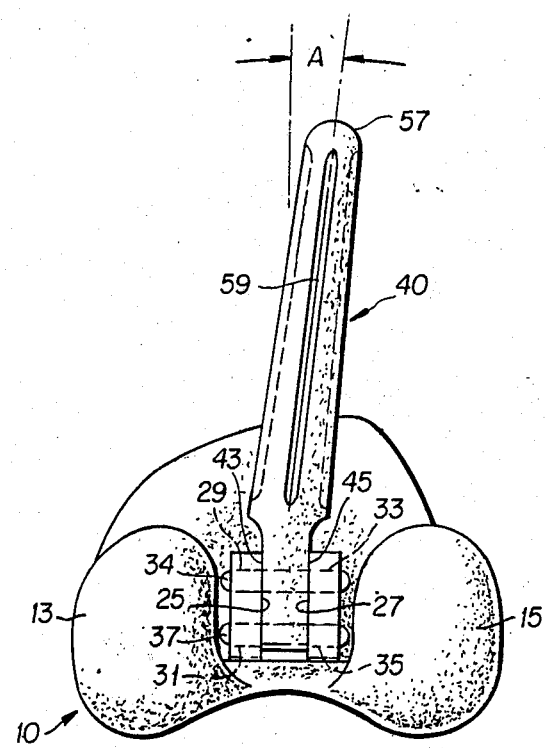
FIG. 3 shows a back view of the prosthesis shown in FIGS. 1 and 2.
Figure 5:
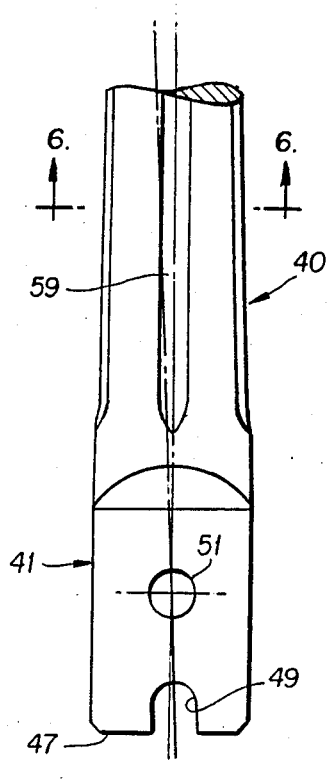
FIG. 5 shows an enlarged view of the modular stem extension of the inventive prosthesis, but from the left side thereof.
Figure 4:
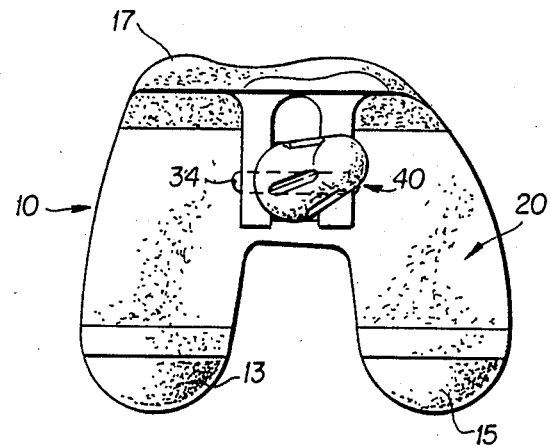
FIG. 4 shows a top view of the prosthesis shown in FIGS. 1-3.

As best seen with reference to FIGS. 3 and 8, the stem 55 of the modular stem extension 40 has a six-degree valgus inclination A which is reversible for left and right patients. Thus, in FIG. 3, the stem extension 40 is seen as mounted on a right-hand femoral knee prosthesis. Were the stem extension 40 to be attached to a left-hand femoral knee prosthesis, before insertion into the left-hand femoral knee prosthesis (not shown), the extension 40 would be rotated 180 degrees about the axis 42 until the valgus inclination is facing in the opposite direction to that which is shown in FIG. 3. Figure 8 shows a modular stem extension 40' which is shown to illustrate the fact that in each of the modular stem extension embodiments of the present invention, a valgus inclination like that which is included in the stem extension 40 is provided.

With particular reference to FIGS. 1, 2, 3 and 5, it is seen that the shank 41 has attached thereto the elongated stem 55 having its largest diameter adjacent the shank 41 and being slightly tapered throughout its length until termination at a rounded end 57. Throughout most of the length of the stem 55, a plurality of circumferentially spaced longitudinal recesses 9 are formed therein to best facilitate fixation of the stem into bone tissue and to provide recesses for the ingrowth of bony tissue, or fixation of bone cement.

As stated above, FIG. 8 shows a modular stem extension designated by the reference numeral 40'. The modular stem extension 40' is so designated because it is intended to convey the fact that all embodiments of modular stem extension in accordance with the teachings of the present invention have a similar degree of approximent valgus inclination.

FIGS. 7, 9 and 10 show three embodiments of modular stem extension having different degrees of superior/inferior angulation. Of course, each of the stem extensions illustrated in FIGS. 7, 9 and 10 include the same valgus inclination as shown with reference to FIG. 8.

FIG. 7 shows a modular stem extension 40a having a shank 41a with a hole 51a therethrough as well as an arculate slot 49a formed therein. As seen in FIG. 7 the hole 51a and the slot 49a are aligned along an axis a of the component 40a. In the modular prosthetic stem component 40a, there is no inferior or superior angulation and, in this respect, the component 40a is termed "neutral".

With reference to FIG. 9, the modular prosthetic stem 25 component 40b is seen to include a shank 41b, a stem 55b, a hole 51b and an arcuate slot 49b. The axis of the component 40b is designated by the reference letter b. It is of note that the slot 49b is displaced laterally from the axis b of the component 40b in a direction such that a line drawn through the centers of the slot and hole displaces an angle B with respect to the axis b of the component 40b. This relationship between the respective positions of the hole 51b and slot 49b will result in either left inferior angulation of the stem 40b or, if reversed, will result in right superior angulation. The angle B may be 1–5 degrees, although 2 degrees is optimal.

With reference to FIG. 10, a modular stem prosthetic component 40c is seen to include a shank 41c, a stem 55c, a hole 51c and a slot 49c. The axis of the component 40c is generally designated by the reference letter c. As seen in FIG. 10, the slot 49c is laterally spaced with respect to the hole 51c with regard to the longitudinal axis c of the component 40c so that a line drawn between the centers of the hole and slot subtends an angle with respect to the axis c of the component 40c of B, but in the direction opposite to the direction of the angle B as shown in FIG. 9. Again the angle B may be 1–5 degres, although 2 degrees is optimal. With the relationship between the hole 51c and the slot 49c as shown in FIG. 10, the component 40c will provide either left superior angulation or, when reversed, will provide right inferior angulation.

Thus, it is seen that with three modular stem prosthesis components 40a, 40b and 40c, as well as two femoral knee prosthesis components, the component designated by the reference numeral 10 for a right-hand knee and the component (not shown) for the left-hand knee, all different combinations of inferior and superior inclination, left and right knee, and valgus inclination may be provided. This is far superior to known prosthesis systems in the prior art, wherein six different complete prostheses would be necessitated at great expense. When consideration is given to the different sizes of prostheses which are manufactured for different sized knees, the significance of the present invention becomes even clearer. Whereas, in known prosthesis systems, to account for the various sizes of the components over one hundred prostheses must be maintained in inventory, through the teachings of the present invention, fewer than twenty pieces would have to be kept in inventory to perform the same function.

As such, an invention has been disclosed in terms of the preferred embodiments thereof which fulfill each and every one of the objects of the present invention as set forth hereinabove and provide a new and improved universal modular prosthesis stem extension of great utility which will result in savings of storage space, inventory and expense by surgeons and hospitals.

Of course, various changes, modifications and alterations in the teachings of the present invention may be contemplated by those skilled in the art without departing from the intended spirit and scope of the present invention. As such, it is intended that the present invention only be limited by the terms of the following claims.

I claim:

1. A modular prosthesis systems comprising:
   (a) a prosthetic head having an undersurface;
   (b) mounting means on said undersurface including at least one flat surface;
   (c) a plurality of diverse stem extensions, each stem extension having a shank with a flat surface complementary to the flat surface of said mounting means; and an elongated stem portion connected to its respective shank defining an obtuse angular relationship between said shank and a longitudinal axis of said stem portion; and
   (d) attachment means for fixedly attaching a said shank to said mounting means;
   (e) said shank being attachable to said mounting means in at least two diverse fixed orientations wherein each said stem portion is connected to its respective shank at an angular relationship corresponding with an inclination of a bone which said stem is intended to be inserted.

2. The invention of claim 1, wherein each stem extension is reversible and said attachment means is provided for installation on either a left-hand or right-hand prosthetic head mounting means.

3. The invention of claim 2, wherein one of said stem portions is connected to its respective shank parallel to said longitudinal axis in the superior/inferior direction.

4. The invention of claim 2, wherein one of said stem portions is connected to its respective shank with left inferior angulation reversible to right superior angulation.

5. The invention of claim 2, wherein one of said stem portions is connected to its respective shank with left superior angulation reversible to right inferior angulation.

6. The invention of claim 1, wherein said mounting means includes two flat surfaces spaced apart to slidingly receive said shank.

7. The invention of claim 6, wherein said attachment means comprises aligned holes in said surfaces and a hole in each said shank alignable therewith, and a pin insertable through said holes to lock a said stem extension on said prosthetic head.

8. The invention of claim 7, wherein each said shank includes an end with a slot therein, said mounting means including a projection insertable into said slot to further lock said stem extension on said prosthetic head.

9. The invention of claim 8, wherein said projection comprises a further pin.

10. The invention of claim 2, wherein said valgus inclination is 6 degrees.

11. The invention of claim 4, wherein said left inferior angulation and right superior angulation is from 1–5 degrees.

12. The invention of claim 5, wherein said left superior angulation and right inferior angulation is from 1–5 degrees.

13. The invention of claim 1, wherein said prosthetic head comprises a femoral head knee joint prosthesis.

14. The invention of claim 1, wherein each said stem portion is tapered from a larger diameter adjacent a respective said shank to a smaller diameter termination remote therefrom.

15. The invention of claim 14, wherein each said stem portion includes a plurality of circumferentially spaced elongated recesses.

16. The invention of claim 1, wherein said prosthetic head comprises a tibial prosthetic head for a knee joint prosthesis system.

* * * * *